(12) United States Patent
Jiang et al.

(10) Patent No.: US 7,722,816 B2
(45) Date of Patent: May 25, 2010

(54) DETECTION DEVICE AND METHOD

(75) Inventors: Hongrui Jiang, Madison, WI (US); Sudheer S. Sridharamurthy, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 263 days.

(21) Appl. No.: 11/753,167

(22) Filed: May 24, 2007

(65) Prior Publication Data

US 2008/0292503 A1 Nov. 27, 2008

(51) Int. Cl.
*G01N 21/00* (2006.01)
(52) U.S. Cl. .................. 422/82.05; 422/56; 422/58; 422/61; 422/62; 422/99; 204/412; 204/424; 73/31.02; 435/4; 435/6; 435/7.1
(58) Field of Classification Search ............ None
See application file for complete search history.

(56) References Cited

U.S. PATENT DOCUMENTS

| 5,071,526 | A | * | 12/1991 | Pletcher et al. | .......... 205/782.5 |
| 2003/0096310 | A1 | * | 5/2003 | Hansen et al. | ................ 435/7.1 |
| 2006/0198761 | A1 | * | 9/2006 | Tokhtuev et al. | ......... 422/82.05 |
| 2009/0074611 | A1 | * | 3/2009 | Monzyk et al. | ................ 422/29 |

* cited by examiner

*Primary Examiner*—Jill Warden
*Assistant Examiner*—Sally A Sakelaris
(74) *Attorney, Agent, or Firm*—Boyle Fredrickson, S.C.

(57) ABSTRACT

A detection device and method for detecting the presence of an agent in a fluid. The device includes a membrane having first and second sides. The membrane allows a stimulus, e.g. ultraviolet light, to dissolve in response to presence of the agent. A source is positioned on a first side of the membrane. The source sources the stimulus toward the membrane. A detection structure is disposed on the second side of the membrane for detecting the stimulus. The detection structure generates an output voltage in response to the intensity of the stimulus detected. As the membrane dissolves, the intensity of the stimulus detected changes.

14 Claims, 2 Drawing Sheets

DETECTION DEVICE AND METHOD

REFERENCE TO GOVERNMENT GRANT

This invention was made with United States government support awarded by the following agencies: NAVY/ONR N-00014-04-1-0659. The United States government has certain rights in this invention.

FIELD OF THE INVENTION

This invention relates generally to bioagent detection systems, and in particular, to a real time, bioagent detection device and method that incorporates a microsensor for sensing bioagents in both the air and aqueous environments.

BACKGROUND AND SUMMARY OF THE INVENTION

Potential biological attacks against large scale civilian populations have become an important issue in homeland security. By way of example, the anthrax cases in the United States in 2001 and the ricin case on Capitol Hill in 2004 have proven that the threat of a biological attack is real. In order to thwart any potential biological attack, the development of a civilian biodefense plan is crucial. Consequently, there has been an enormous effort to develop practical and efficient biosensors in recent years.

Most present biosensors take advantage of biologically active materials for high sensitivity and selectivity. In general, the biosensor includes a biorecognition structure (e.g., a membrane) in contact with or interrogated by a transducer. The biologically active material recognizes a particular biological molecule through a reaction, specific adsorption, or other physical or chemical process, and the transducer converts the output of this recognition into a usable signal, usually electrical or optical. Many approaches have been explored to achieve ultra-sensitive detection of bio-species. These biodetection approaches can be categorized as either an engineering-oriented approach or a biological-oriented approach. In other words, most biodetection schemes are either based on relatively complex electronic, photonic and/or electrochemical methods or more elegant biomolecular methods (e.g. enzyme linked immunosorbent assay, or ELISA) typically with an optical or spectrometry-based readout.

By way of example, one process utilizes photonics integrated on a microchip to study the interaction between the optical field and the target bio-analyte. Because most biorecognition processes occur in an aqueous ambient, this approach requires the integration of photonics, highly sensitive microelectronics and microfluidic systems on a single microchip. The use of ion-channel switches as biosensors has also been explored, but the bioelectronic interface is a delicate one. Often, when an approach promises very high sensitivity, the output signal from the biorecognition is very small, thus requiring extremely highly-sensitive on-chip microelectronics for signal amplification, processing and wireless transmission. The high demand of these approaches on system integration and high sensitivity photonics and electronics circuitry presents a big challenge to the biosensors in terms of cost, reliability and power consumption. The more biomolecular based approaches, like ELISA, are simple, but typically require a macro scale spectrometry system to quantify the output.

Therefore, it is a primary object and feature of the present invention to provide a bioagent detection device that is highly sensitive and selective.

It is a further object and feature of the present invention to provide a bioagent detection device that is small in size and weight and is inexpensive to manufacture.

It is a still further object and feature of the present invention to provide a bioagent detection device that provides continuous monitoring of a user selected environment.

In accordance with the present invention, a detection device is provided for detecting the presence of an agent in a fluid. The device includes a membrane having first and second sides. The membrane allows passage of a stimulus therethrough in response to presence of the agent. A source is positioned on a first side of the membrane. The source sources the stimulus toward the membrane. A detection structure is disposed on the second side of the membrane for detecting the stimulus.

The detection device includes a body that defines a first chamber for accommodating the membrane therein. The membrane is fabricated from a polymeric material that dissolves in response to exposure to the agent. The source includes an ultraviolet light emitting diode for generating ultraviolet light having an intensity. The ultraviolet light is the stimulus. The detection structure includes an ultraviolet light detector. The ultraviolet light detector generates an output voltage in response to the intensity of the ultraviolet light detected. A mask is positioned between the source and the detection structure. The mask prevents passage of the stimuli therethrough.

In accordance with a further aspect of the present invention, a detection device is provided for detecting the presence of an agent in a fluid. The detection device includes a body defining a chamber. The chamber accommodates the flow of fluid therein. A membrane is disposed in the chamber of the body. The membrane allows for the passage of a stimulus therethrough in response to presence of the agent in the chamber. A source is positioned on a first side of the body. The source directs the stimulus toward the membrane. A detection structure is disposed on the second side of the body for detecting the stimulus.

The stimulus is ultraviolet light and the source includes an ultraviolet light emitting diode for generating the ultraviolet light. The detection structure includes an ultraviolet light detector. The ultraviolet light detector generates an output voltage in response to the intensity of the ultraviolet light detected. The membrane is fabricated from a polymeric material that dissolves in response to exposure to the agent. A mask is positioned between the source and the detection structure. The mask prevents passage of the stimulus therethrough. The body includes an upper surface and lower surface. The chamber extends through the body and the mask is coated on the lower surface of the body. It is contemplated for the ultraviolet light to be at a predetermined wavelength and for the membrane to have a different absorption of light than the fluid at the predetermined wavelength.

In accordance with a further aspect of the present invention, a method of detecting the presence of an agent in a fluid is provided. The method includes the steps of engaging a membrane with the fluid and generating a signal in response to detection of a stimulus directed at the membrane.

The membrane is formed from a polymeric material that dissolves in response to exposure to the agent. The step of generating a signal includes the additional steps of directing the stimulus having an intensity at the membrane and detecting the stimulus. An output voltage is generated in response to the intensity of the stimulus detected. The stimulus is directed toward a first side of the membrane and the stimulus is detected on a second side of the membrane.

The method may also include the additional steps of positioning the membrane in a chamber of a microfluidic device and flowing the fluid through the chamber. The stimulus is ultraviolet light at a predetermined wavelength. The membrane has a different absorption of light than the fluid at the predetermined wavelength.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
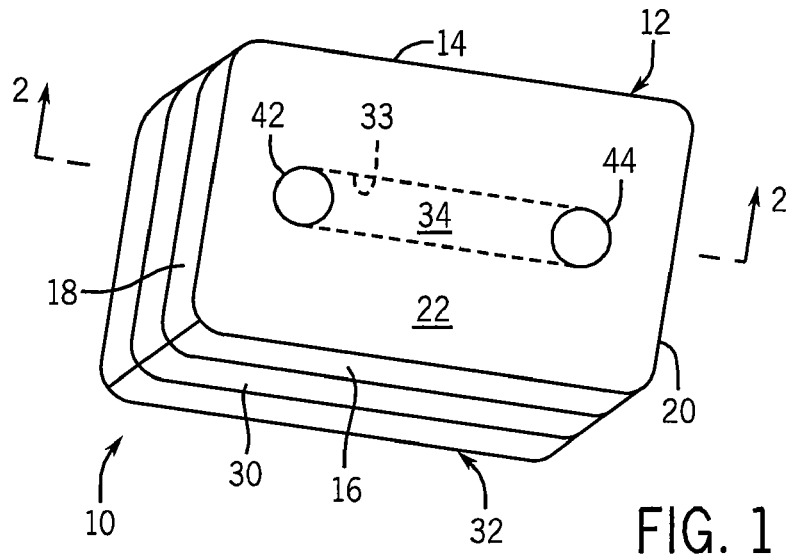
FIG. 1 is an isometric view of a detection device in accordance with the present invention.

Referring to FIGS. 1-4, a detection device for use in the method of the present invention is generally designated by the reference numeral 10. Detection device 10 includes cartridge 12 formed from any suitable material, such as polydimethylsiloxane (PDMS). Cartridge 12 has first and second sides 14 and 16, respectively, and first and second ends 18 and 20, respectively. Cartridge 12 further includes upper and lower surfaces 22 and 24, respectively. Lower surface 24 of cartridge 12 includes central portion 29 vertical spaced from outer periphery 31 by sidewall 33.

Figure 2:
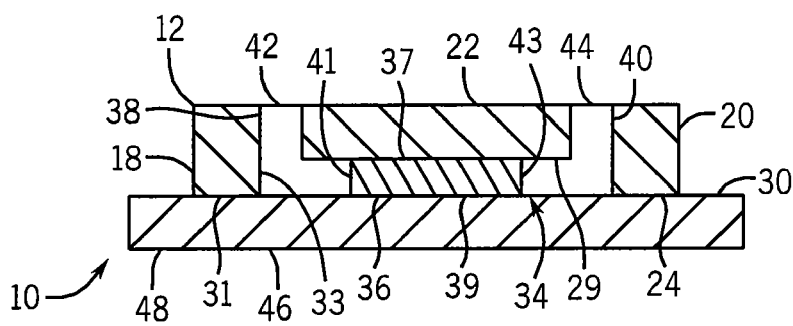
FIG. 2 is a cross-sectional view of the detection device of the present invention taken along line 2-2 of FIG. 1.
Figure 3:
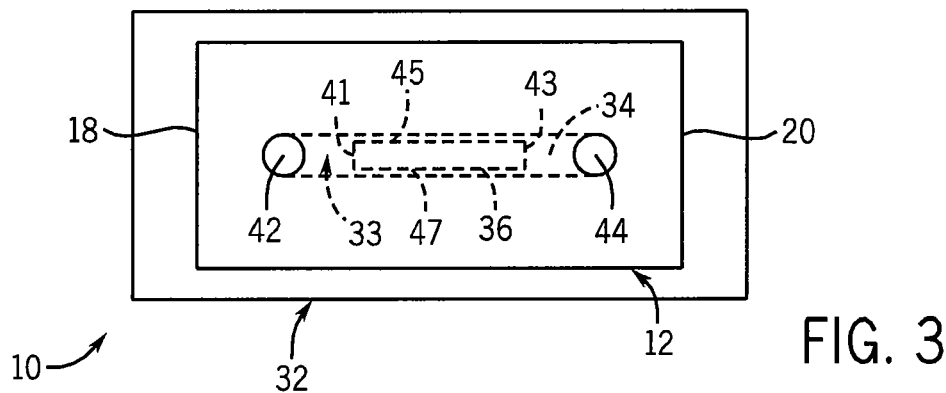
FIG. 3 is a top plan view of the detection device of FIG. 1.

Cartridge 12 is positioned on upper surface 30 of microscope slide 32. It can be appreciated that in addition to being positionable on microscope slide 32, cartridge 12 may be positioned on an alternate substrate, without deviating from the scope of the present invention. An adhesive or a gasket 27, FIG. 5, may be used to affix outer periphery 31 of lower surface 24 of cartridge 12 to upper surface 30 of microscopic slide 32. When assembled, sidewall 33 and lower surface 24 of cartridge 12 and upper surface 30 of microscope slide 32 define chamber 34 for receiving membrane 36. Membrane 36 includes upper surface 37 in engagement with central portion 29 of lower surface 24 of cartridge 12 and lower surface 39 in engagement with upper surface 30 of microscope slide 32. Upper and lower surfaces 37 and 39, respectively, of membrane 36 are interconnected by first and second ends 41 and 43, respectively, and first and second sides 45 and 47, respectively. As best seen in FIG. 2, sides 45 and 47 of membrane 36 are spaced from sidewall 33 of lower surface to allow for the flow of fluid therepast. For reasons hereinafter described, in the preferred embodiment, membrane 36 is fabricated from a chemically sensitive polymeric material that dissolves in response to exposure to a predetermined agent or analyte.

Cartridge 12 further includes input and output channels 38 and 40, respectively, therethrough. Input channel 38 has input port 42 at a first end thereof that communicates with upper surface 22 of cartridge 12 and a second end communicating with chamber 34. Output channel 40 has output port 44 at a first end thereof that communicates with upper surface 22 of cartridge 12 and a second end communicating with chamber 34. It can be appreciated that input and output channels 38 and 40, respectively, are interconnected by and communicate with chamber 34. The dimensions of input and output channels 38 and 40, respectively, and chamber 34 are arbitrary.

Figure 4:
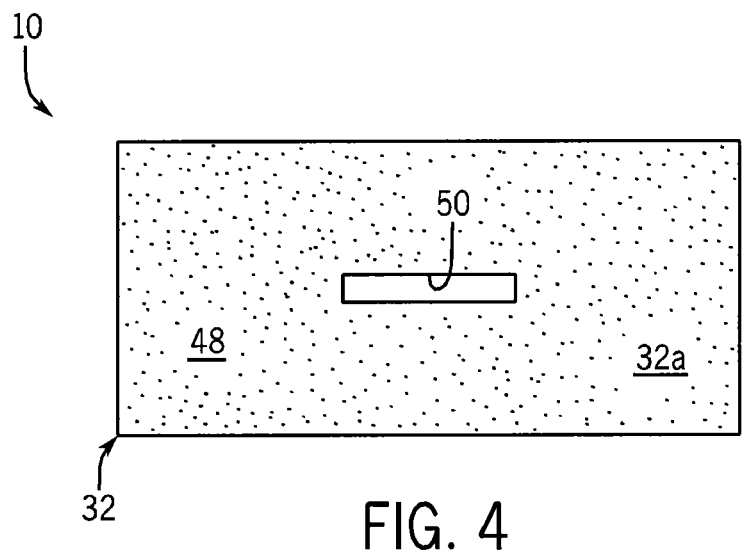
FIG. 4 is a bottom plan view of the detection device of FIG. 1.

Referring to FIG. 4, it is contemplated to pattern mask 46 on lower surface 48 of microscope slide 32. However, mask 46 may be patterned on the upper surface 30 of microscope slide 32, FIG. 5, without deviating from the scope of the present invention. Mask 46 includes central opening 50 therein that corresponds in size and shape to the outer periphery of membrane 36 and that is aligned with membrane 36. It is intended for mask 46 to prevent the passage of a predetermined stimulus, such as ultraviolet light, from passing through microscope slide 32 in those portions 32a of microscope slide 32 not in axial alignment with membrane 36. By way of example, mask 46 may take the form of a coating on lower surface 48 of microscope slide 32. The coating may include a first titanium layer sputtered on lower surface 48 of microscopic slide 32. A copper layer is deposited on the first titanium layer and a second titanium layer is deposited on the copper layer. The first titanium layer serves as an adhesive layer for the copper layer and the second titanium layer prevents oxidation of the copper layer.

In order to fabricate detection device 10, coating is sputtered on lower surface 48 of microscope slide 32, as heretofore described. Thereafter, central opening 50 is etched into the coating to provide mask 46. Central opening 50 in mask 46 corresponds in size and shape to the desired size and shape of membrane 36. Once mask 46 is formed on lower surface 48 of microscope slide 32, cartridge 12 is fixed to upper surface 30 of microscope slide 32 as heretofore described. Utilizing input port 42 of input channel 38, chamber 34 is filled with a poly(acrylamide) based, pre-hydrogel solution, e.g., a solution including a monomer such as acrylamide, a crosslinker such as cystaminebisacrylamide, a photoinitiator such as (4-benzoylbenzyl)trimethyl-ammonium chloride, a co-initiator such as N-methyl-diethanolamine, and a solvent such as water combined in a ratio of (by weight): 0.15:0.00374:0.02:0.02:1. The partially constructed detection device 10 is now flipped vertically so that mask 46 is on top. The pre-hydrogel solution does not drain from chamber 34 though input and output channels 38 and 40, respectively, due to the surface tension of the pre-hydrogel solution at input and output ports 42 and 44, respectively. Cartridge 12 is exposed to ultraviolet light of a predetermined intensity, e.g., 18 mW/cm$^2$, for a predetermined time period, e.g., 150 seconds. Mask 46 prevents polymerization of a first portion of the pre-hydrogel solution within chamber 34 that is not axially aligned with central opening 50. However, the pre-hydrogel solution in chamber 34 that is axially aligned with central opening 50 polymerizes in response to exposure to the ultraviolet light so as to form membrane 36. Thereafter, the unpolymerized pre-hydrogel solution is flushed from chamber 34 with ethanol. The device is then baked, e.g. on a hotplate, at a predetermined temperature, e.g., 50° Celcius, for a predetermined time period, e.g., 5 minutes. As described, it can be appreciated that membrane 36 is self-aligned with central opening 50 in mask 46, for reasons hereinafter described.

As is known, poly(acrylamide) (PAAm) hydrogels dissolve in a response to the presence of a reducing agent. For example, it has been shown that disulfide cross-linked PAAm hydrogels disintegrate in the presence of dithiothreitol (DTT). Consequently, it can be appreciated that membrane 36 may be used as a sensing element in detection device 10. The presence of the reducing agent breaks the bonds of the hydrogel used to form membrane 36 thereby rendering it porous and eventually completely dissolved. The dissolution time of membrane 36 depends mainly on the physical dimensions of membrane 36, as well as, the concentration of the reducing agent. Higher concentrations of the reducing agent break more bonds of the hydrogel in a given interval of time, and hence, show a quicker response.

Figure 5:
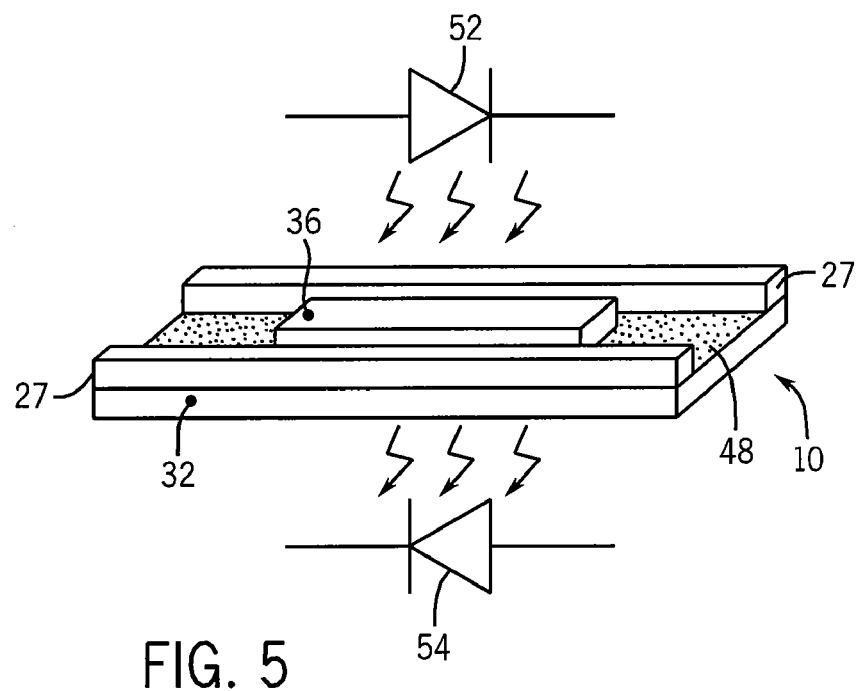
FIG. 5 is a schematic view of the detection device of the present invention.

Referring to FIG. 5, it is intended for detection device 10 to perform a temporal measurement of the optical absorption of membrane 36 in the presence of the sample solution. Absorption may be characterized by the Beer-Lambert law:

$$I_T = I_O \exp(-\alpha L) \quad \text{Equation (1)}$$

wherein: $I_T$ is the intensity of transmitted light; $I_O$ is the intensity of the incident light; $\alpha$ is the absorption coefficient of the absorbing material (either membrane 36 or the sample solution); and L is the absorption path length.

The change in the intensity of transmitted light $I_T$ is attributed to two reasons: 1) Diffusion of the sample into the hydrogel membrane soon after introducing the sample solution into chamber 34; and 2) Dissolution of membrane 36 if the sample solution contains a predetermined reducing agent or analyte, as hereinafter described. After microfabrication of membrane 36, the hydrogel from which membrane 36 is fabricated is in a dehydrated state and has a relatively high absorption of the incident light as compared to the hydrated state. Upon introduction of the sample solution into chamber 34 of detection device 10, the sample solution diffuses into membrane 36 and causes a change in the absorption of the membrane, and hence, the intensity of transmitted light $I_T$. Presence of the reducing agent or analyte in the sample solution dissolves and replaces membrane 36, thereby resulting in a further change in the intensity of transmitted light $I_T$. The difference in the intensity of transmitted light $I_T$ may be used to sense the dissolution of membrane 36, and hence, the presence of the analyte.

In operation, detection device 10 is coupled to a micropositioner (not shown) and aligned to an ultraviolet light source, e.g., an ultraviolet light emitting diode (UV-LED) 52, and an ultraviolet light photodetector 54. Photodetector 54 provides an output voltage proportional to the intensity of the UV radiation incident on its detecting surface. After detection device 10 is positioned, a sample solution is introduced into chamber 34 in any conventional manner, such as through input port 42 of input channel 38 of cartridge 12 using a micropipette. UV-LED 52 sources ultraviolet light 52 onto membrane 36 and photodetector 54 provides an output voltage proportional to the intensity of light transmitted through membrane 36. Mask 46 blocks ultraviolet light from passing through any portion of detection device 10 except membrane 36. As membrane 36 is dissolved and replaced by the sample solution, the output voltage of photodetector 54 increases. Once the dissolution of membrane 36 is complete, the output voltage of photodetector 54 saturates at a particular value. It is noted that in order to obtain a significant change in the output voltage of photodetector 54 upon dissolution of membrane 36, it is necessary for UV-LED 52 to employ a wavelength at which the difference between the light absorption of membrane 36 and that of the sample solution is a maximum.

It has been found that the dissolution characteristics of membrane 36, and thus the output voltage of photodetector 54, depend on the concentration of the predetermined analyte in the sample solution. Consequently, the dissolution characteristics for a host of analyte concentrations and the associated output voltages of photodetector 54 over time can be determined. Thereafter, by monitoring output voltages of photodetector 54 and the dissolution characteristics of a membrane in response to an unknown concentration of an analyte in a sample solution, a best-fit estimate of the concentration of the analyte in the sample solution can be made.

Various modes of carrying out the invention are contemplated as being within the scope of the following claims particularly pointing and distinctly claiming the subject matter that is regarded as the invention.

We claim:

1. A detection device for detecting the presence of an agent in a fluid, comprising:
   a membrane having first and second sides, the membrane:
      allowing passage of a stimulus therethrough in response to presence of the agent; and
      dissolving in response to the agent;
   a source positioned on a first side of the membrane, the source sourcing the stimulus toward the membrane; and
   a detection structure disposed on the second side of the membrane for detecting the stimulus, the detection structure generating a signal in response to the intensity of the stimulus detected;
   wherein a concentration of the agent in the fluid may be determined in response to a variance of the signal over time.

2. The detection device of claim 1 further comprising a body defining a first chamber for accommodating the membrane therein.

3. The device of claim 1 wherein the membrane is fabricated from a polymeric material that dissolves in response to exposure to the agent.

4. The device of claim 1 wherein the source includes an ultraviolet light emitting diode for generating ultraviolet light having an intensity.

5. The device of claim 4 wherein the ultraviolet light is the stimulus and wherein the detection structure includes an ultraviolet light detector, the ultraviolet light detector generating an output voltage in response to the intensity of the ultraviolet light detected.

6. The device of claim 1 further comprising a mask positioned between the source and the detection structure, the mask preventing passage of the stimulus therethrough.

7. A detection device for detecting the presence of an agent in a fluid, comprising:
   a body defining a chamber, the chamber accommodating the flow of fluid therein;
   a membrane disposed in the chamber of the body, the membrane:
      allowing passage of a stimulus therethrough in response to presence of the agent in the chamber; and
      dissolving in response to the agent;
   a source positioned on a first side of the body, the source directing the stimulus toward the membrane; and
   a detection structure disposed on the second side of the body for detecting the stimulus, the detection structure generating a signal in response to the intensity of the stimulus detected;
   wherein a concentration of the agent in the fluid may be determined in response to a variance of the signal over time.

8. The device of claim 7 wherein the stimulus is ultraviolet light.

9. The device of claim 7 wherein the source includes an ultraviolet light emitting diode for generating ultraviolet light having an intensity.

10. The device of claim 9 wherein the ultraviolet light is the stimulus and wherein the detection structure includes an ultraviolet light detector, the ultraviolet light detector generating an output voltage in response to the intensity of the ultraviolet light detected.

11. The device of claim 7 wherein the membrane is fabricated from a polymeric material that dissolves in response to exposure to the agent.

12. The device of claim 7 further comprising a mask positioned between the source and the detection structure, the mask preventing passage of the stimulus therethrough.

13. The device of claim 7 wherein:
the body includes an upper surface and lower surface;
the chamber extends through the body; and
the mask is coated on the lower surface of the body.

14. The device of claim 7 wherein the stimulus is ultraviolet light at a predetermined wavelength and wherein the membrane has a different absorption of light than the fluid at the predetermined wavelength.

* * * * *